United States Patent
Ye et al.

(10) Patent No.: US 7,945,012 B2
(45) Date of Patent: May 17, 2011

(54) COMPUTED TOMOGRAPHY IMAGE ACQUISITION

(75) Inventors: Jinghan Ye, Fremont, CA (US); John F. Vesel, Kirtland, OH (US); Michael J. Petrillo, Pleasanton, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 193 days.

(21) Appl. No.: 12/377,302

(22) PCT Filed: Jul. 24, 2007

(86) PCT No.: PCT/US2007/074201
§ 371 (c)(1), (2), (4) Date: Feb. 12, 2009

(87) PCT Pub. No.: WO2008/021671
PCT Pub. Date: Feb. 21, 2008

(65) Prior Publication Data
US 2010/0232565 A1   Sep. 16, 2010

Related U.S. Application Data

(60) Provisional application No. 60/822,678, filed on Aug. 17, 2006.

(51) Int. Cl.
*G01N 23/00* (2006.01)

(52) U.S. Cl. .............................................. 378/11; 378/14
(58) Field of Classification Search .............. 378/21–27, 378/4, 11, 14
See application file for complete search history.

(56) References Cited

U.S. PATENT DOCUMENTS

| | | | |
|---|---|---|---|
| 5,319,693 A | 6/1994 | Eberhard et al. | |
| 2003/0108146 A1 | 6/2003 | Malamud | |
| 2004/0013225 A1 | 1/2004 | Gregerson et al. | |
| 2004/0077088 A1 | 4/2004 | Charles, Jr. et al. | |
| 2004/0170254 A1 | 9/2004 | Gregerson et al. | |
| 2004/0264636 A1* | 12/2004 | Claus et al. | 378/26 |
| 2005/0078785 A1* | 4/2005 | Endo | 378/22 |
| 2005/0259783 A1 | 11/2005 | Hoffman | |
| 2008/0310584 A1 | 12/2008 | Hey et al. | |

FOREIGN PATENT DOCUMENTS

| | | |
|---|---|---|
| DE | 102005004502 A1 | 8/2006 |
| WO | 0062674 A1 | 10/2000 |
| WO | 2005009206 A2 | 2/2005 |

OTHER PUBLICATIONS

Feldkamp et al., Practical cone-beam algorithm, J. Opt. Soc. Am. A, Jun. 1984, pp. 612-619, vol. 1, No. 6, Optical Society of America.
Ge Wang, X-ray micro-CT with a displaced detector array, Medical Physics, Jul. 2002, pp. 1634-1636, vol. 29, No. 7, Am. Assoc. Phys. Med.
Gregor et al., Conebeam X-Ray Computer Tomography With an Offset Detector Array, IEEE, 2003, pp. 803-806.
Gregor et al., Support Algorithms for X-ray Micro-CT Conebeam Imaging, Proceedings of the International Meeting on Fully Three-Dimensional Image Reconstruction in Radiology and Nuclear Medicine, Saint Malo, France, Jul. 2003, Four pages.

* cited by examiner

*Primary Examiner* — Hoon Song

(57) ABSTRACT

A computed tomography acquisition geometry provides an increased field of view (218). A radiation source (202, 702) such as an x-ray source and a radiation detector (204, 704) are displaced from the imaging center (214). In one implementation, the central ray (216) of a radiation beam (212) is parallel to the plane of the detector (204, 704) at the detector midpoint (219, 719), but is displaced from the imaging center.

29 Claims, 6 Drawing Sheets

COMPUTED TOMOGRAPHY IMAGE ACQUISITION

CROSS REFERENCE TO RELATED APPLICATIONS

This application claims the benefit of U.S. provisional application Ser. No. 60/822,678 filed Aug. 17, 2006, which is incorporated herein by reference.

The present application relates to computed tomography (CT). It finds particular application to x-ray CT for medical applications. It also finds application to article and security inspection, non-destructive testing, pre-clinical imaging, and other situations in which CT data can provide useful information about the structure or function of an object.

One area in which CT imaging systems have gained widespread acceptance is in medicine, where CT scanners are widely used by radiologists and other medical professionals in connection with the diagnosis and treatment of disease. The relatively recent adoption of multi-slice systems has further broadened the clinical application range of CT systems.

Figure 1A:
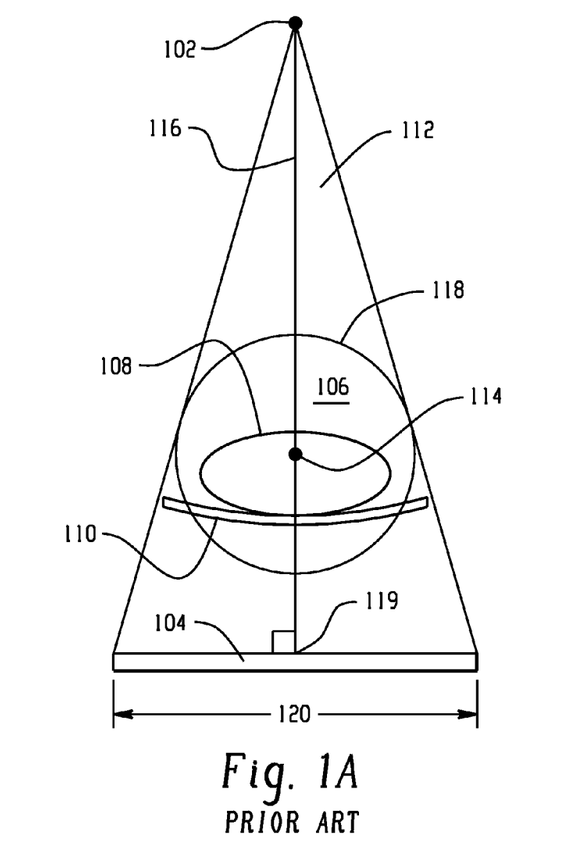
FIG. 1A is a transaxial view of a prior art full beam CT acquisition geometry.

The data acquisition geometry of a conventional third generation x-ray CT system having a flat panel detector is shown in FIG. 1A. FIG. 1A depicts a transaxial plane of a system, for example a central plane of a cone-beam system. An x-ray source 102 and an x-ray sensitive detector 104 are disposed on opposite sides of an examination region 106 and radially displaced from a center of rotation 114. A human patient or other object to be examined 108 is supported in the examination region 106 by a suitable support 110. The source 102 emits radiation 112 which traverses the examination region 106 and is detected by the detector 104 as the source 102 and detector 104 rotate about a center of rotation 114.

In the illustrated full beam acquisition geometry, a central ray or projection 116 of the x-ray beam 112 intersects the center of rotation 106 and is perpendicular to the detector transverse center 119. The detector transverse dimension 120 is such that the detector 104 detects radiation 112 which has traversed the entire transverse FOV 118 at each projection angle. Thus, a complete angular sampling of the transverse FOV requires that data be collected over approximately 180° plus the x-ray beam 114 transverse fan angle. While illustrated in relation to a flat panel detector, it will also be appreciated that the full beam acquisition geometry is applicable to systems in which the detector 104 is generally arcuate.

However, it is generally desirable to reduce the physical size of the detector required to achieve a given transverse FOV. For example, relatively larger detectors tend to be more complex and expensive to manufacture. Moreover, the size of the available detector arrays can be a limiting factor in the system design. These considerations become increasingly acute with the increasing popularity of multi-slice systems, and particularly as the relatively larger multi-slice detectors become a greater portion of the total system cost.

Figure 1B:
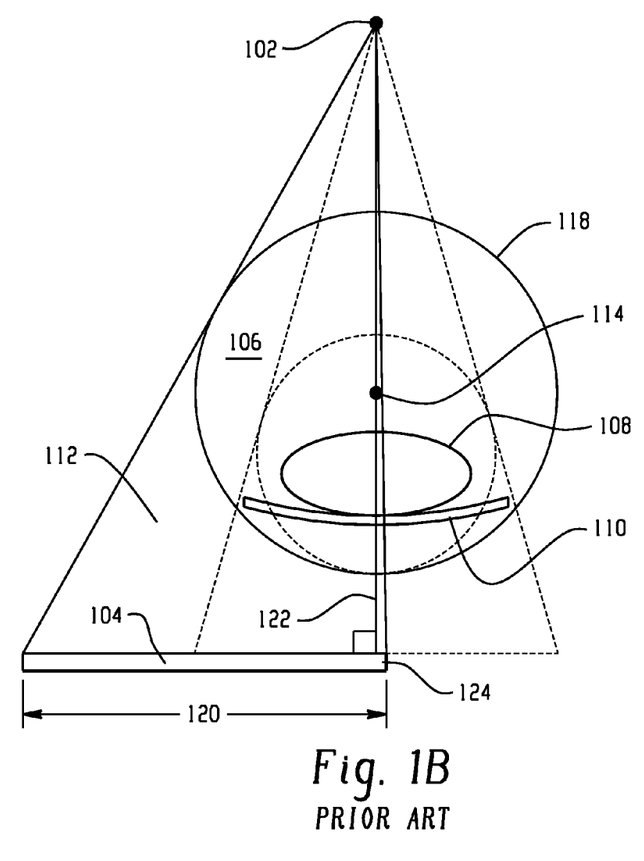
FIG. 1B is a transaxial view of a prior art half beam CT acquisition geometry.

With reference to FIG. 1B, a half beam acquisition geometry has also been proposed. See, e.g., Gregor, et al., *Cone-beam X-ray Computed Tomography with an Offset Detector*, IEEE 2003 (2003); Wang, et al., *X-ray Micro-CT with a Displaced Detector Array*, Med. Phys. 29 (7), July 2002; Lin, et al., *Half Field of View Reduced-Size CT Detector*, PCT publication WO 00/62647, dated 26 Oct. 2000.

Relative to the full beam geometry, the detector 104 is shifted in the transverse direction by approximately one-half its transverse dimension 120. A ray or projection 122 which intersects the center of rotation 114 is perpendicular to the plane of the detector 104. At a given projection angle, the detector 104 detects radiation which has traversed approximately one-half the transverse FOV 118 (note that an overlap or transition region 124 ensures that projection data is acquired at a central region of the transverse FOV 118). While the half beam acquisition geometry achieves a relatively larger transverse FOV relative to the full beam geometry (which is illustrated for comparative purposes by the dashed lines in FIG. 1B), complete angular sampling of the transverse FOV requires that data be collected over an angular range of approximately 360°. Moreover, such a system requires that the lamallae or septa of the anti-scatter grid extend in the transverse direction, or the use of a special asymmetric anti-scatter grid.

Consequently, there remains room for improvement. For example, it is desirable to further improve the detector utilization while maintaining a suitable image quality. It is also desirable to simplify system construction.

Aspects of the present invention address these matters, and others.

In accordance with one aspect of the present invention, an apparatus acquires tomographic projection data at a plurality of angular positions relative to an object disposed in an examination region. The apparatus includes a radiation source and a radiation sensitive detector which detects radiation emitted by the source and which has traversed the examination region. Both the source and a transverse center of the detector are transversely displaced from the center of a transverse field of view during acquisition of the projection data.

According to another aspect, a computed tomography method includes emitting radiation from a location which is transversely displaced from a center of a transverse field of view. The radiation traverses a portion of the transverse field of view. The method also includes using a radiation detector to acquire computed tomography projection data indicative of the radiation. The detector is transversely displaced from the center of the transverse field of view. The method also includes repeating the steps of emitting radiation and using the radiation detector to acquire computed tomography projection data indicative of the radiation at each of a plurality of projection angles to acquire a CT data set, and reconstructing the CT data set to generate volumetric data.

According to another aspect, a computed tomography apparatus includes an x-ray source, an x-ray detector, and a reconstructor. The x-ray source is transversely displaced from and rotates about a center of rotation. The x-ray detector detects radiation emitted by the x-ray source and is transversely displaced from the center of rotation. The x-ray detector rotates about the center of rotation in a fixed mechanical relation to the x-ray source so as to acquire projection data at a plurality of projection angles. The x-ray source emits radiation having a transverse fan angle, and a complete angular sampling of a transverse field of view requires the acquisition of projection data over an angular range greater than 180° plus the fan angle. The reconstructor reconstructs the projection data to generate volumetric data indicative of the transverse field of view.

Still further aspects of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

Figure 2:
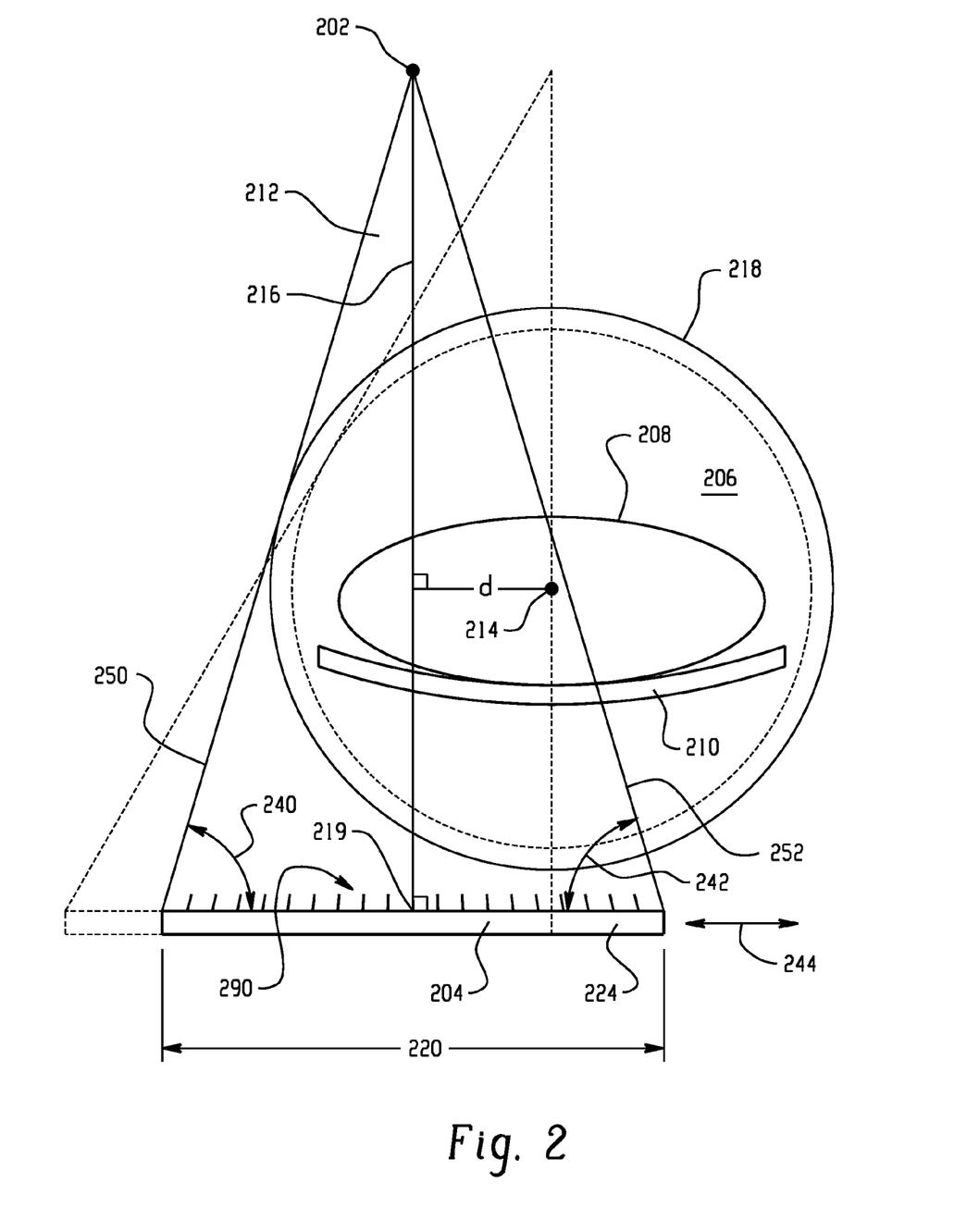
FIG. 2 is a transaxial view of a displaced CT acquisition geometry.

An improved, double displaced CT acquisition geometry in which both the source and detector are displaced from the imaging isocenter is shown in FIG. 2. As illustrated, a couch or other suitable object support 210 supports an object under examination 208 in an examination region 206. An x-ray source 202 such as an x-ray tube and an x-ray sensitive detector 204 such as a flat panel area detector array extending in the transverse and axial directions rotate about a center of rotation 214, which also serves as the center of the transverse FOV 218. A central ray or projection 216 of the x-ray beam 212 is perpendicular to the detector transverse center 219 but is displaced from the center of rotation 214.

An anti-scatter grid 290 is disposed between the detector 204 and the examination region 206 so as to reduce scatter radiation received by the detector 204. The grid 290 includes a plurality of lamellae focused on the source 202 such that the grid is transversely symmetric with respect to the transverse detector center 219. As will be appreciated, such symmetry simplifies system construction. Two dimensional (2D) anti-scatter grids, for example grids laving lamallae extending in both the transverse and axial directions, may also be implemented.

As illustrated, the minimum displacement between the central ray 216 and the isocenter 214 is the distance d. The transverse displacement of the detector 204 is selected to minimize the maximum acceptance angle for radiation received by the detector 204. Where the detector 204 is a flat panel detector, the incidence angles 240, 242 at which the outermost rays 250, 252 of the x-ray beam 212 intersect the detector 204 are equal. As illustrated, a transition region 224 is also provided.

The transverse FOV 218 is larger than that of a comparable half beam acquisition geometry, which is depicted in dashed line in FIG. 2 for illustrative purposes. For a given detector transverse dimension 220 and radial distance between the source 202 and the center of rotation 214, the size of the transverse FOV 218 can be varied by varying the distance d between the central ray 216 and the center of rotation 214. The case where the central ray 216 intersects the center of rotation 214 (i.e., where d=0) corresponds to the full beam geometry of FIG. 1A. In the maximum FOV configuration, a rotation of approximately 360° is required to obtain a complete angular sampling, whereas a rotation of 180° plus the fan or cone angle provides a complete angular sampling when configured in the full beam geometry. The required angular range for intermediate configurations varies between 180° plus the fan angle and 360° and can readily be calculated.

Figure 3:
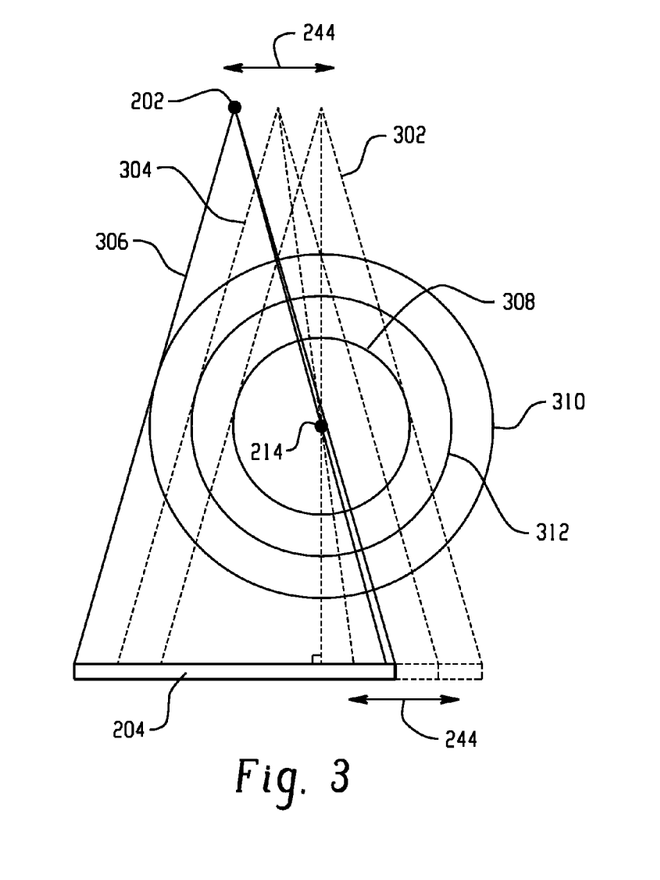
FIG. 3 is a transaxial view of a CT acquisition geometry showing a source and detector are displaced in relation to an imaging region.

The described acquisition geometry can be implemented in various ways. With reference to FIG. 3, both the source 202 and detector 204 are shifted in a direction 244 parallel to the plane of the detector 204 while keeping the imaging center and center of rotation 214 unchanged from that of a comparable full or half beam acquisition geometry. The object under examination 208, object support 210, and anti-scatter grid 290 are omitted from FIG. 3 for clarity of illustration.

As illustrated, the direction of the displacement 244 is tangential to the transverse FOV. FIG. 3 shows the source 202 and detector 204 shifted to exemplary first 302, second 304, and third 306 positions. The first position 302 corresponds to the full beam acquisition geometry of FIG. 1A. It provides the smallest transverse FOV 308, and a complete data set is acquired over an angular range of 180° plus the fan or cone angle. The third position 306 provides the largest transverse FOV 310; a complete data set is acquired over an angular range of approximately 360°. The second position 304 depicts an arbitrary intermediate position which provides an intermediate transverse FOV 312; data is likewise acquired over an intermediate angular range. While the source 202 and detector 204 are shown in multiple positions to illustrate the relative displacement of the source 202 and detector, it will be understood that the source 202 and detector 204 are advantageously maintained in a given position while sampling over the requisite angular range.

Figure 4:
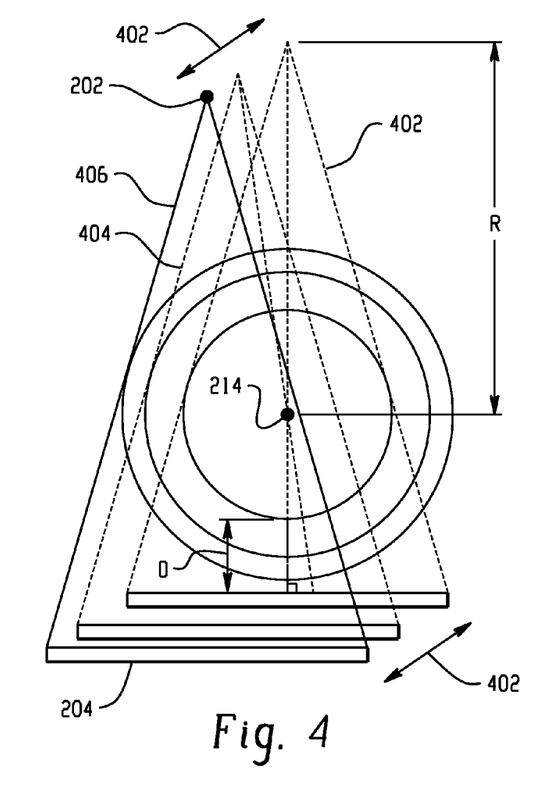
FIG. 4 is a transaxial view of a CT acquisition geometry showing the source and detector displaced relative to an imaging region.

Another technique for providing a displaced acquisition geometry is shown in FIG. 4. As illustrated, both the source 202 and detector 204 are shifted in a direction 302 in which the minimum distance D between the detector 204 and the edge of the transverse FOV remains constant. Again, the source 202 and detector 204 are shown in first 402, second 404, and third 406 positions which provide increasingly larger transverse FOVs. It should also be noted that, as illustrated, the radial displacement R of the source 202 from the center of rotation 214 is relatively greater than that illustrated in FIG. 2. Such an arrangement further increases the transverse FOV.

Figure 5:
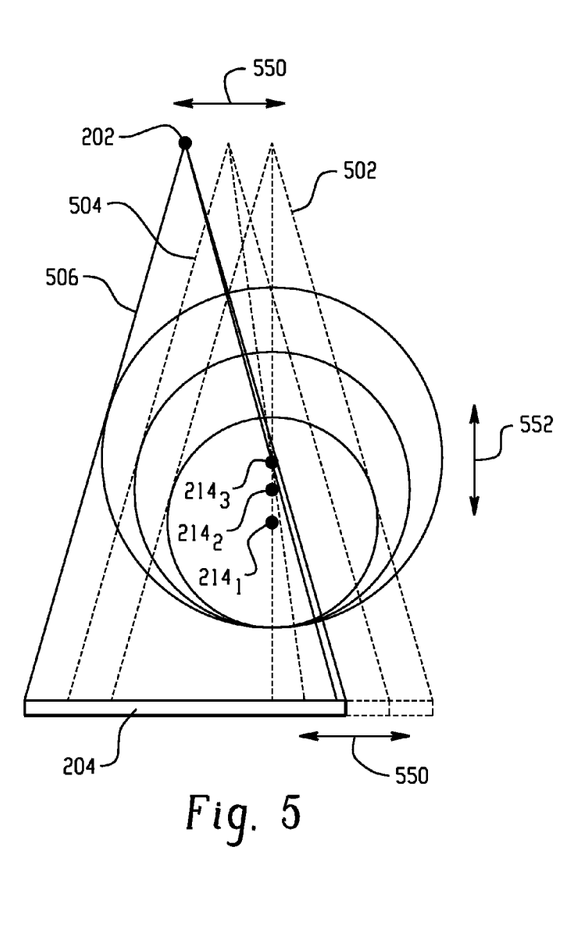
FIG. 5 is a transaxial view of a CT acquisition geometry showing the source and detector displaced in relation to an imaging region.

Yet another technique for providing a displaced acquisition geometry is shown FIG. 5. As illustrated, the source 202 and detector 204 are shifted in a direction 550 tangent to the transverse FOV while the imaging center is displaced in a direction 552 which is perpendicular to the transverse FOV or to the major plane of the detector 204. Again, the source 202 and detector 204 are shown in first 502, second 504, and third 506 positions. The respective first $214_1$, second $214_2$, and third $214_3$ centers of rotation are also shown. As will be appreciated, the illustrated arrangement provides an acquisition geometry identical to that of FIG. 4.

Figure 6:
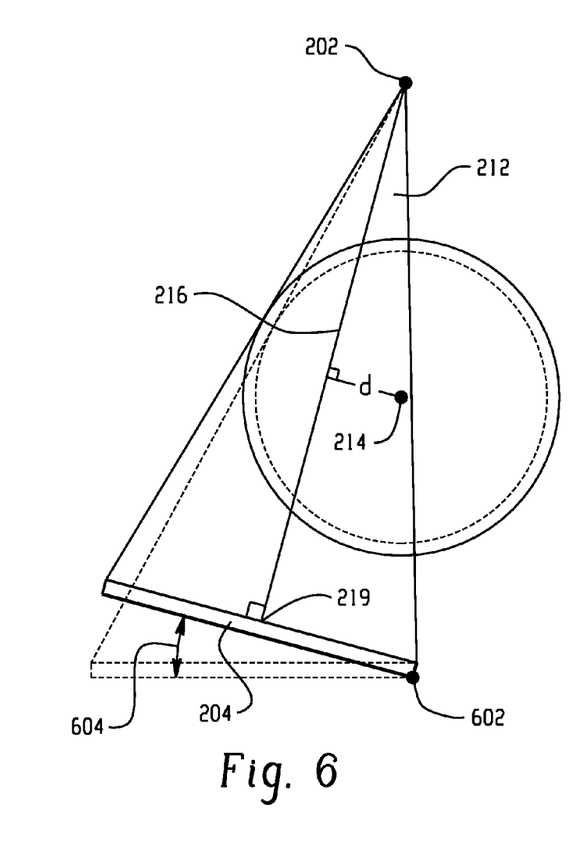
FIG. 6 is a transaxial view of a CT acquisition geometry.

Still another technique for providing a displaced acquisition geometry is shown in FIG. 6. As illustrated, the detector 204 is pivoted about a pivot axis 602 by an angle 604 such that a ray 214 of the x-ray beam 212 which intersects the transverse center 219 of the detector 204 is perpendicular to the plane of the detector 204. The size of the transverse FOV can be adjusted by varying the angle 604 as desired. The case where the angle 604 is zero (0) corresponds to the half beam geometry of FIG. 1B, which is shown in dashed line in FIG. 6 for illustrative purposes.

Figure 7:
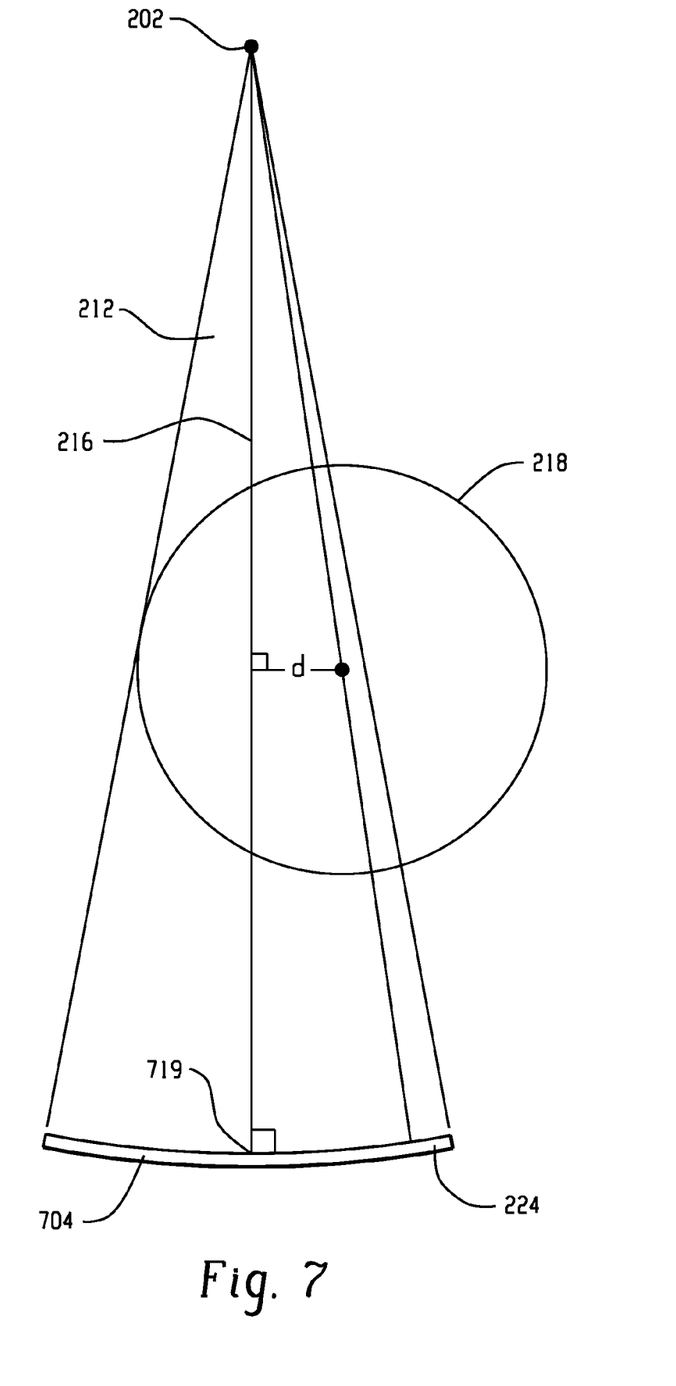
FIG. 7 is a transaxial view of a CT acquisition geometry.

While the foregoing discussion has focused on flat panel detectors, arcuate detectors may also be used. The acquisition geometry for a system having a detector 704 which subtends a portion of a circular arc centered on the transverse position of the x-ray source 202 is shown in FIG. 7. A central ray or projection 216 of the x-ray beam 212 is perpendicular to the tangent of the detector 704 arc at the detector center 719 but is displaced from the center of rotation 206 by a distance d. As illustrated, a transition region 224 is also provided. As will be appreciated by those skilled in the art, the discussion above with respect to FIGS. 2-6 is also applicable to the arcuate detector configuration.

Figure 8:
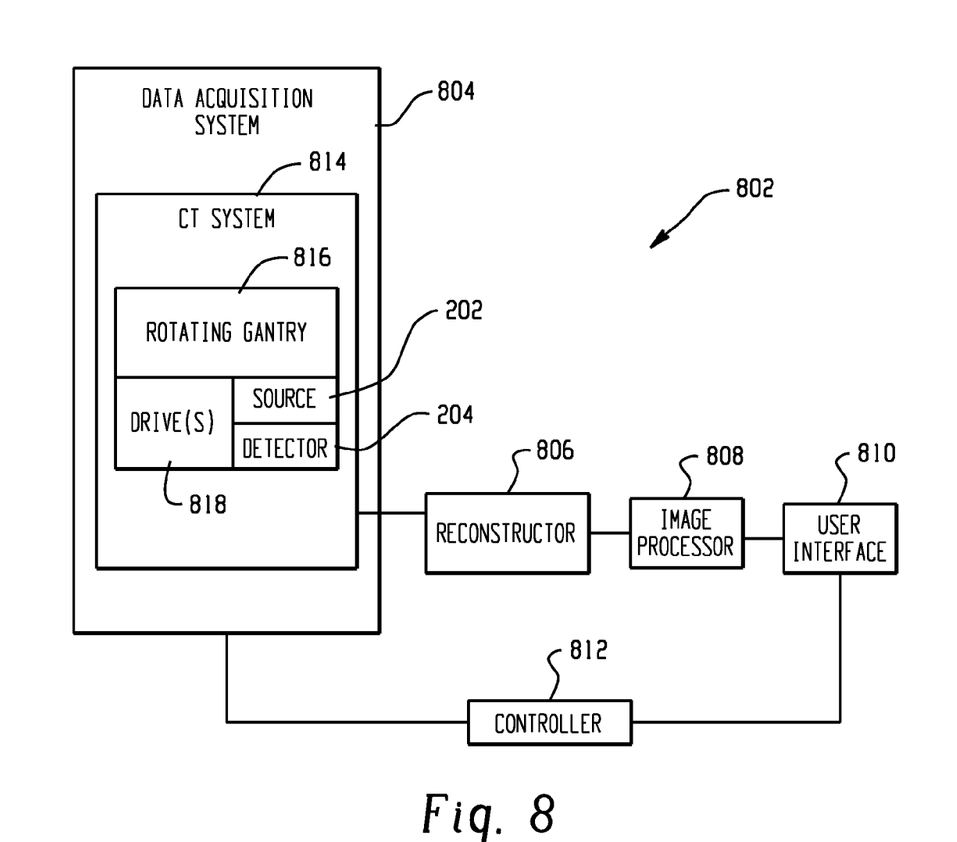
FIG. 8 depicts an imaging system.

FIG. 8 depicts an imaging system 802 suitable for use with the double displaced acquisition geometry. The system 802 includes a data acquisition system 804, a reconstructor 806, image processor 808, a user interface 810, and a controller 812.

The data acquisition system 804 includes a CT data acquisition system 814 in which the source 202 and detector 204 are mounted to a rotating gantry 816 for rotation about the examination region. Circular, 360° or other angular sampling range axial, helical, circle and line, saddle, or other desired scanning trajectories may be implemented, for example by moving the object support 210 longitudinally in coordination with rotation of the rotating gantry 816.

In one implementation, the source 202 and detector 206 are fixedly mounted in relation to the rotating gantry 816 so that the acquisition geometry is fixed. In another, the source 202 and detector are movably mounted to the rotating gantry 816 so that the acquisition geometry is variable, for example to allow the relative movement shown in FIGS. 3-7 above. In such an implementation, one or more drives 818 may provide the requisite motive force.

Alternately, the source 202 and detector 204 may be moved manually by a human user. In either case, the source 202 and detector 204 are advantageously mounted to a common frame or otherwise so that the physical relationship between the source 202 and detector 204 is unchanged from one FOV configuration to another, as doing so reduces the need for separate blank or calibrations scans.

A reconstructor 806 reconstructs the data generated by the data acquisition system 804 using known reconstruction techniques to generate volumetric data indicative of the object under examination. Suitable reconstruction techniques include analytical techniques such as filtered backprojection, as well as iterative techniques. One technique which is well-suited to the reconstruction of cone beam data is the known Feldkamp algorithm. Where the acquisition geometry provides a transition region 224, a smoothing function may be employed to reduce the effects of redundant data in the transition region 224.

An image processor 808 processes the volumetric data as required, for example for display in a desired fashion on a user interface 810, which may include one or more output devices such as a monitor and printer and one or more input devices such as a keyboard and mouse.

The user interface 810, which is advantageously implemented using software instructions executed by a general purpose or other computer so as to provide a graphical user interface (GUI), allows the user to control or otherwise interact with the imaging system 802, for example by selecting a desired FOV configuration or dimension, initiating and/or terminating scans, selecting desired scan or reconstruction protocols, manipulating the volumetric data, and the like. In one implementation, one or both of the FOV configuration and reconstruction protocol are established automatically by the imaging system 802 based on a scan protocol selected by the user. As yet another example, the user interface 810 may prompt or otherwise allow the user to enter a desired transverse radius, diameter or other FOV dimension. In such an implementation, the information from the user is used to automatically calculate the requisite position(s) of the source 102 and/or detector 104.

A controller 812 operatively connected to the user interface 810 controls the operation of the data acquisition system 704, for example to carry out a desired scan protocol, cause the drive(s) 818 to position the source 102 and/or detector 104 so as to provide the desired FOV, and the like.

Figure 9:
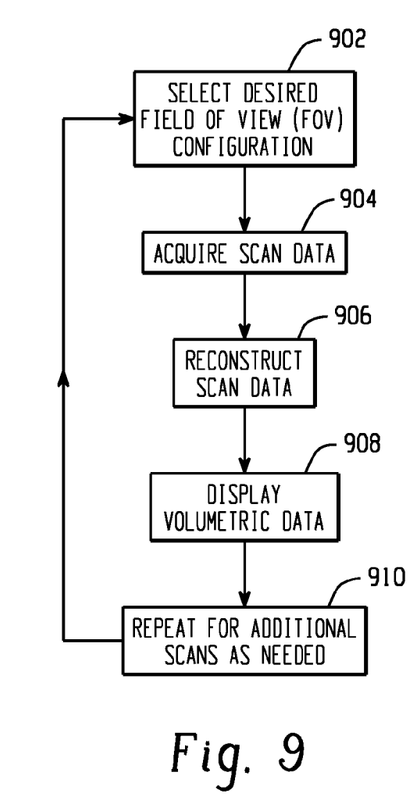
FIG. 9 depicts an imaging method.

Operation of the imaging system 802 will now be described in relation to FIG. 9. In the case of an acquisition system 802 which provides for an adjustable FOV configuration, the positions of the source 202 and detector 204 are adjusted to provide the desired FOV configuration at step 902. By way of one example, adjusting the geometry to provide the largest transverse FOV may be necessary to scan the chest of a large human patient, whereas adjusting the geometry to the full beam configuration may be sufficient to conduct a brain scan.

Scan data is acquired at step 904 so as to acquire projection data at each of a plurality of angular positions about the examination region 206. The angular range required to sample the transverse FOV 206 is again a function of the selected FOV configuration. Note that the positions of the source 202 and detector may remain unchanged during the requisite angular sampling.

The scan data is reconstructed at step 906 and displayed in a desired format at step 908.

At step 910, the process is repeated as desired, for example to scan a succession of patients. Note that additional scan(s) may be obtained prior to reconstructing and/or displaying the data acquired in given scan.

While the foregoing has focused on x-ray CT system in which the source 202 is the focal spot of an x-ray tube and hence substantially a point source, other alternatives are contemplated. For example, the source 202 may be implemented as a line source. Wedge and other beam geometries are also contemplated. Gamma and other radiation sources may also be used. Rather than rotating the source 202 and detector 204 about the examination region 206, the source 202 and detector 204 may remain at a constant angular position while the object 208 is moved and/or rotated to produce the requisite angular sampling. Multiple sources 202 and detectors 204 may also be provided, in which case corresponding sets of sources and detectors may be offset angularly and/or longitudinally from one another. Note that in systems having multiple angularly offset sources and detectors, the rotation required to provide a complete angular sampling range is ordinarily reduced compared to systems having a single source/detector pair, and the trajectory may be adjusted accordingly.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An apparatus for acquiring tomographic projection data at a plurality of angular positions relative to an object disposed in an examination region, the apparatus comprising:
   a radiation source that emits a radiation beam from a first position and a second different position;
   a radiation sensitive detector which detects radiation emitted by the source, which radiation has traversed the examination region;
   wherein both the source and a transverse center of the detector are transversely displaced from a center of a transverse field of view during acquisition of the projection data, and
   wherein from the first position and from the second position, the radiation beam has a generally fan shaped transverse cross section, the cross section includes first and second outermost rays, and the outermost rays intersect the detector at equal angles of incidence.

2. The apparatus of claim 1 including a reconstructor which reconstructs the projection data to generate volumetric data indicative of the object.

3. The apparatus of claim 1 wherein the source and the detector rotate about an axis of rotation and wherein the axis of rotation is the center of the transverse field of view.

4. The apparatus of claim 1 wherein the source emits a radiation beam having a generally fan shaped transverse cross section, wherein the transverse cross section includes a ray which is perpendicular to the detector, and wherein the ray is transversely displaced from the center of the transverse field of view.

5. The apparatus of claim 4 wherein the detector includes a transverse center and the ray intersects the transverse center.

6. The apparatus of claim 4 wherein the ray is a central ray of the radiation beam.

7. The apparatus of claim 4 wherein the detector is a flat panel detector.

8. The apparatus of claim 1 wherein the detector includes a transition region in which the detectors generate redundant projection data.

9. The apparatus of claim 1 including means for varying a position of the source and detector relative to the center of the transverse field of view to provide a full beam acquisition geometry.

10. The apparatus of claim 1 including means for shifting the source and detector in a transverse direction which is parallel to a major plane of the detector.

11. The apparatus of claim 10 including means for displacing the imaging center in a direction which is perpendicular to the transverse field of view.

12. The apparatus of claim 1 including means for shifting the source and the detector in a transverse direction in which a minimum distance between the detector and an edge of the transverse field of view remains constant.

13. The apparatus of claim 1 including means for pivoting the source and detector about a pivot axis so as to vary a size of the transverse field of view.

14. The apparatus of claim 1 including a user interface which receives a user input identifying a desired dimension of the transverse field of view and wherein the apparatus uses the desired dimension to determine a desired position of the detector.

15. The apparatus of claim 1, where the a radiation source is a computed tomography radiation source and where the a radiation sensitive detector is a computed tomography radiation sensitive detector.

16. A computed tomography method comprising:
emitting first radiation from a location which is transversely displaced from a center of a transverse field of view, wherein the first radiation traverses a portion of the transverse field of view;
using a radiation detector to acquire computed tomography projection data indicative of the first radiation, wherein the detector is transversely displaced from the center of the transverse field of view;
repeating the steps of emitting first radiation and using the radiation detector to acquire computed tomography projection data indicative of the first radiation at each of a plurality of projection angles to acquire a first CT data set;
reconstructing the first CT data set to generate first volumetric data.

17. The method of claim 16 further including:
following the step of using a radiation detector to acquire computed tomography projection data indicative of the first radiation, varying the transverse displacement of the location and the transverse displacement of the detector so as to vary a size of the transverse field of view;
emitting second radiation, wherein the second radiation traverses at least a portion of the transverse field of view;
using the radiation detector to acquire computed tomography projection data indicative of the second radiation;
repeating the steps of emitting second radiation and using a radiation detector to acquire computed tomography projection data indicative of the second radiation at each of a plurality of projection angles to acquire a second CT data set;
reconstructing the second projection data set to generate second volumetric data.

18. The method of claim 17 wherein the second projection data traverses the entire transverse field of view.

19. The method of claim 17 wherein varying the transverse displacement includes shifting the source and the detector in a transverse direction which is tangent to the transverse field of view.

20. The method of claim 17 wherein varying the transverse displacement includes shifting the source and the detector in a direction in which a minimum distance between the detector and an edge of the transverse field of view remains constant.

21. The method of claim 16 including
receiving a user input which identifies a desired dimension of the transverse field of view;
using the desired dimension to determine a desired position of the detector.

22. The method of claim 16 wherein the radiation detector is a flat panel detector, emitting first radiation includes emitting a radiation beam having a generally fan shaped transverse cross section, wherein the transverse cross section includes first and second outermost rays, and wherein the outermost rays intersect the detector at equal angles of incidence.

23. The method of claim 16 wherein emitting first radiation includes emitting a radiation beam having a generally fan shaped transverse cross section, wherein the cross section includes a central ray, the central ray is transversely displaced from the center of the transverse field of view, and the central ray intersects the detector at an angle which is perpendicular to the detector.

24. The method of claim 16 including rotating the location and the radiation detector about an axis of rotation, wherein the axis of rotation is the center of the transverse field of view.

25. A computed tomography apparatus comprising:
an x-ray source, wherein the x-ray source is transversely displaced from and rotates about a center of rotation;
an x-ray detector, wherein the x-ray detector detects radiation emitted by the x-ray source, wherein the x-ray detector is transversely displaced from the center of rotation and rotates about the center of rotation in a fixed mechanical relation to the x-ray source so as to acquire projection data at a plurality of projection angles, wherein the x-ray source emits radiation having a transverse fan angle, and wherein a complete angular sampling of a transverse field of view requires the acquisition of projection data over an angular range greater than 180° plus the fan angle;
a reconstructor which reconstructs the projection data to generate volumetric data indicative of the transverse field of view.

26. The apparatus of claim 25 wherein the apparatus includes a rotating gantry and wherein the x-ray source and the x-ray detector are movably mounted in relation to the rotating gantry.

27. The apparatus of claim 25 wherein a central ray of the radiation emitted by the x-ray source is displaced from the center of rotation and intersects a transverse center of the x-ray detector.

28. The apparatus of claim 25 including means for varying the transverse displacement of the x-ray detector so as to vary a size of the transverse field of view.

29. The apparatus of claim 25 including means for acquiring data according to one of a circular, circle and line, helical, or saddle trajectory.

* * * * *